US008920794B2

(12) United States Patent  (10) Patent No.: US 8,920,794 B2
Stassen et al.  (45) Date of Patent: Dec. 30, 2014

(54) METHOD FOR TREATING FILTRATION FAILURE AFTER TRABECULECTOMY SURGERY

(71) Applicant: ThromboGenics NV, Heverlee/Leuven (BE)

(72) Inventors: Jean-Marie Stassen, Lubbeek (BE); Ingeborg Stalmans, Knokke (BE)

(73) Assignee: ThromboGenics NV, Heverlee (BE)

( * ) Notice: Subject to any disclaimer, the term of this patent is extended or adjusted under 35 U.S.C. 154(b) by 76 days.

(21) Appl. No.: 13/968,775

(22) Filed: Aug. 16, 2013

(65) Prior Publication Data

US 2013/0330318 A1  Dec. 12, 2013

Related U.S. Application Data

(63) Continuation of application No. 13/392,623, filed as application No. PCT/EP2010/062584 on Aug. 27, 2010, now abandoned.

(60) Provisional application No. 61/237,723, filed on Aug. 28, 2009.

(30) Foreign Application Priority Data

Aug. 28, 2009 (EP) .................................. 09168912

(51) Int. Cl.
| A61K 38/48 | (2006.01) |
| A61K 9/00 | (2006.01) |
| A61K 47/12 | (2006.01) |
| A61K 45/06 | (2006.01) |

(52) U.S. Cl.
CPC ............. *A61K 38/484* (2013.01); *A61K 9/0048* (2013.01); *A61K 9/0051* (2013.01); *A61K 47/12* (2013.01); *A61K 45/06* (2013.01)
USPC .................................................... 424/94.64

(58) Field of Classification Search
CPC .......................... A61K 9/0048; A61K 9/0051
USPC ...................................................... 424/94.64
See application file for complete search history.

(56) References Cited

U.S. PATENT DOCUMENTS

| 4,774,087 | A | 9/1988 | Wu et al. |
| 5,288,489 | A | 2/1994 | Reich et al. |
| 5,304,118 | A | 4/1994 | Trese et al. |
| 5,304,383 | A | 4/1994 | Eibl et al. |
| 5,407,673 | A | 4/1995 | Reich et al. |
| 5,520,912 | A | 5/1996 | Eibl et al. |
| 5,597,800 | A | 1/1997 | Eibl et al. |
| 5,776,452 | A | 7/1998 | Eibl et al. |
| 6,355,243 | B1 | 3/2002 | Novokhatny et al. |
| 6,585,972 | B2 | 7/2003 | Peyman |
| 6,733,750 | B1 | 5/2004 | Peyman |
| 6,787,135 | B2 | 9/2004 | Trese et al. |
| 6,899,877 | B2 | 5/2005 | Peyman |
| 6,946,438 | B1 | 9/2005 | Nagai et al. |
| 6,964,764 | B2 | 11/2005 | Zimmerman et al. |
| 6,969,515 | B2 | 11/2005 | Jesmok et al. |
| 7,445,775 | B2 | 11/2008 | Collen et al. |
| 7,544,500 | B2 | 6/2009 | Bradley et al. |
| 7,547,435 | B2 | 6/2009 | Pakola et al. |
| 7,776,026 | B2 | 8/2010 | Trese et al. |
| 7,803,368 | B2 | 9/2010 | Pakola et al. |
| 7,867,489 | B2 | 1/2011 | Pakola et al. |
| 7,871,608 | B2 | 1/2011 | Zimmerman et al. |
| 7,914,783 | B2 | 3/2011 | Pakola et al. |
| 8,034,913 | B2 | 10/2011 | Hunt et al. |
| 8,101,394 | B2 | 1/2012 | Novokhatny |
| 8,182,808 | B2 | 5/2012 | Novokhatny |
| 8,231,869 | B2 | 7/2012 | Scuderi, Jr. et al. |
| 8,268,782 | B2 | 9/2012 | Rebbeor et al. |
| 8,383,105 | B2 | 2/2013 | Pakola et al. |
| 8,420,079 | B2 | 4/2013 | Hunt et al. |
| 8,460,655 | B2 | 6/2013 | Pakola et al. |
| 8,512,980 | B2 | 8/2013 | Novokhatny |
| 2004/0081643 | A1 | 4/2004 | Peyman |
| 2007/0212358 | A1 | 9/2007 | Bartels |
| 2007/0231352 | A1 | 10/2007 | Tsai |
| 2011/0300123 | A1 | 12/2011 | Pakola et al. |
| 2013/0164273 | A1 | 6/2013 | Zimmerman et al. |
| 2013/0164815 | A1 | 6/2013 | Dadd et al. |
| 2013/0195887 | A1 | 8/2013 | Pakola et al. |
| 2013/0202613 | A1 | 8/2013 | Pakola et al. |
| 2013/0302304 | A1 | 11/2013 | Pakola et al. |

FOREIGN PATENT DOCUMENTS

| EP | 0 009 879 | 4/1980 |
| EP | 0 480 906 | 4/1992 |
| EP | 0 631 786 | 1/1995 |
| EP | 1 117 437 | 7/2001 |

(Continued)

OTHER PUBLICATIONS

Mehta et al. (British Journal of Opthalmology, vol. 84, p. 983-986, 2000).*
Lee et al. (Journal of Ocular Pharmacology and Therapeutics, vol. 11, No. 3, p. 227-232, 1995).*
Newsome et al. (Investigative Opthalmology, vol. 10, No. 6, p. 424-429, 1971).*
Addicks et al., "Histologic characteristics of filtering blebs in glaucomatous eyes," *Arch Ophthalmol.*, 101:795-798 (1983).

(Continued)

*Primary Examiner* — Sharmila G. Landau
*Assistant Examiner* — Damon B Bowe
(74) *Attorney, Agent, or Firm* — Fish & Richardson P.C.

(57) ABSTRACT

The current invention relates to the improvement of trabeculectomy surgery. The improvement more specifically resides in an extended lifetime of the sclera-corneal drainage channel created by trabeculectomy surgery. The improvement is obtained by post-surgical administration of a plasmin or active derivative thereof in the form of topical eye drops alone, by anterior chamber injection alone, or by any combination of these.

22 Claims, 3 Drawing Sheets

(56) References Cited

FOREIGN PATENT DOCUMENTS

Figure 2:
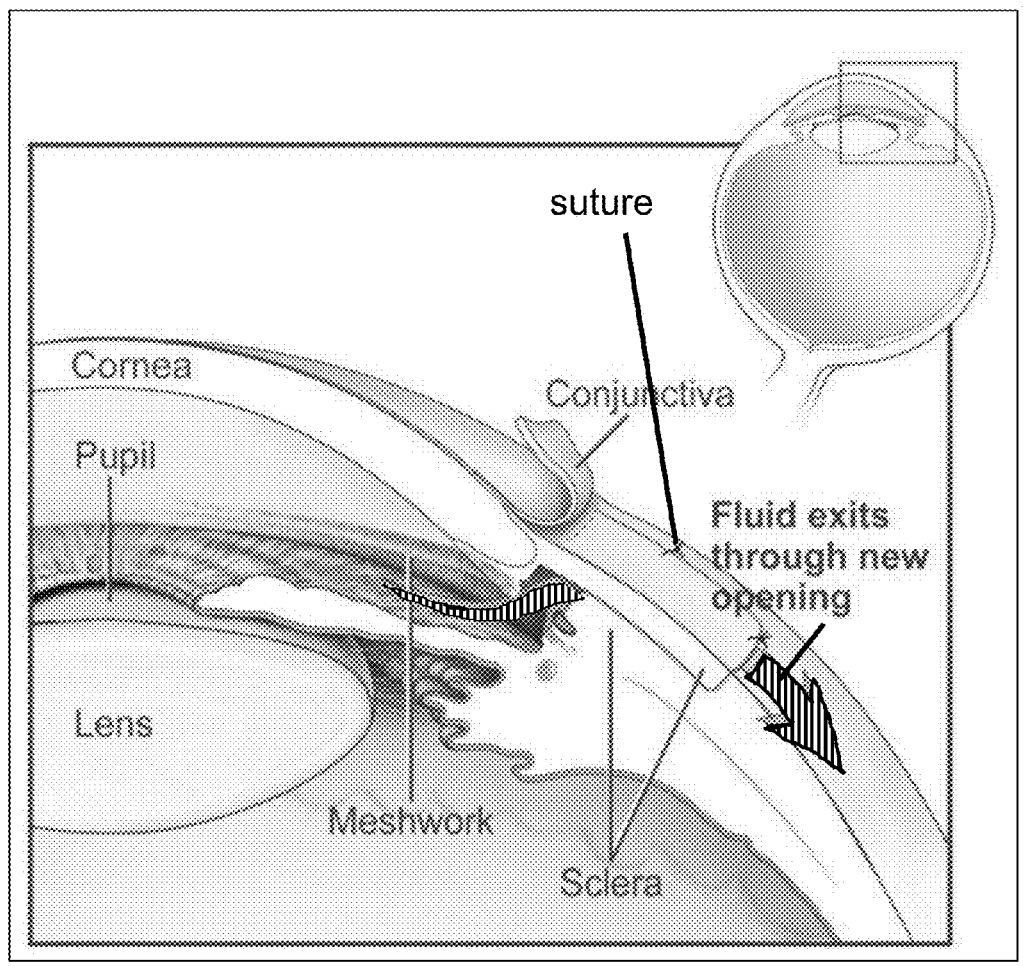

| EP | 1 232 251 | 8/2002 |
|---|---|---|
| EP | 1 232 252 | 8/2002 |
| EP | 1 232 254 | 8/2002 |
| EP | 1 343 903 | 9/2003 |
| EP | 1 581 254 | 10/2005 |
| EP | 1 740 698 | 1/2007 |
| EP | 2 327 415 | 6/2011 |
| EP | 2 327 416 | 6/2011 |
| GB | 2 393 121 | 3/2004 |
| WO | WO 89/01336 | 2/1989 |
| WO | WO 93/07893 | 4/1993 |
| WO | WO 93/15189 | 8/1993 |
| WO | WO 97/01631 | 1/1997 |
| WO | WO 00/18436 | 4/2000 |
| WO | WO 01/04269 | 1/2001 |
| WO | WO 01/36608 | 5/2001 |
| WO | WO 01/36609 | 5/2001 |
| WO | WO 01/36611 | 5/2001 |
| WO | WO 02/50290 | 6/2002 |
| WO | WO 02/078564 | 10/2002 |
| WO | WO 03/033019 | 4/2003 |
| WO | WO 2004/052228 | 6/2004 |
| WO | WO 2005/016455 | 2/2005 |
| WO | WO 2005/105990 | 11/2005 |
| WO | WO 2006/122249 | 11/2006 |
| WO | WO 2007/047874 | 4/2007 |
| WO | WO 2007/070390 | 6/2007 |
| WO | WO 2007/078761 | 7/2007 |
| WO | WO 2007/101005 | 9/2007 |
| WO | WO 2008/026999 | 3/2008 |
| WO | WO 2009/067407 | 5/2009 |
| WO | WO 2009/073457 | 6/2009 |
| WO | WO 2009/073471 | 6/2009 |
| WO | WO 2011/004011 | 1/2011 |
| WO | WO 2011/023805 | 3/2011 |
| WO | WO 2012/093132 | 7/2012 |
| WO | WO 2013/024074 | 2/2013 |

OTHER PUBLICATIONS

Astrup et al., "The fibrin plate method for estimating fibrinolytic activity," *Arch Biochem. Biophys.*, 346-351 (1952).
Burr et al., "Medical versus surgical interventions for open angle glaucoma," *Cochrane Database Syst. Rev.*, 18(2):CD004399 (2005).
Castellino et al., "Rabbit plasminogen and plasmin isozymes," *Methods Enzymol.*, 45:273-286 (1976).
CAT-152 0102 Trabeculectomy Study Group, Khaw et al., "A phase III study of subconjunctival human anti-transforming growth factor beta(2) monoclonal antibody (CAT-152) to prevent scarring after first-time trabeculectomy," *ophthalmology*, 114:1822-1830 (2007).
Christensen et al., "Enzymic properties of the neo-plasmin-Val-422 (miniplasmin)," *Biochim. Biophys. Acta*, 567:472-481 (1979).
Christensen et al., "Stopped-flow fluorescence kinetics of bovine alpha 2-antiplasmin inhibition of bovine midiplasmin," *Biochem J.*, 305:97-102 (1995).
Cordeiro et al., "Novel antisense oligonucleotides targeting TGF-beta inhibit in vivo scarring and improve surgical outcome," *Gene Ther.*, 10:59-71 (2003).
Database Biosis [Online] Biosciences Information Service, Philadelphia, PA, US (1995), Tomoko et al., "Effect of tissue plasminogen activator on re-elevated intraocular pressure in the early postoperative period after trabeculectomy" XP002561743, Database accession No. PREV199598458175, & GANKA, 49(6):1201-1205 (1995) ISSN: 0370-5579.
Deacon et al., "Technetium 99m-plasmin: a new test for the detection of deep vein thrombosis," *Br. J. Radiol.*, 53:673-677 (1980).
Deutsch et al., "Plasminogen: purification from human plasma by affinity chromatography," *Science*, 170:1095-1096 (1970).
Gandorfer, "Enzymatic vitreous disruption," *Eye*, 22:1273-1277 (2008).
Gillies et al., Cytokines, fibrosis and the failure of glaucoma filtration surgery, *Aust. NZ J. Ophthalmol.*, 19:299-304 (1991).

Greenfield et al., "Late-onset bleb leaks after glaucoma filtering surgery," *Arch. Ophthalmol.*, 116:443-447 (1998).
Hitchings, "Initial treatment for open-angle glaucoma—medical, laser, or surgical? Surgery is the treatment of choice for open-angle glaucoma," *Arch Ophthalmol.*, 116:241-242 (1998).
Hitchings et al., "Clinico pathological correlation in eyes with failed fistulizing surgery," *Trans. Ophthalmol. Soc. UK*, 103:84-88 (1983).
Hosseini et al., "IL-1 and TNF induction of matrix metalloproteinase-3 by c-Jun N-terminal kinase in trabecular meshwork," *Invest Ophthalmol. Vis. Sci.*, 47:1469-1476 (2006).
Hunt et al., "Simplified recombinant plasmin: production and functional comparison of a novel thrombolytic molecule with plasma-deprived plasmin," *Thromb. Haemost.*, 100(3):413-419 (2008).
Jampel et al., "Cellular proliferation after experimental glaucoma filtration surgery," *Arch. Ophthalmol.*, 106:89-94 (1988).
Katz et al., "Mitomycin C versus 5-fluorouracil in high-risk glaucoma filtering surgery. Extended follow-up," *Ophthalmology*, 102:1263-1269 (1995).
King et al., "Frequency of bleb manipulations after trabeculectomy surgery," *Br. J. Ophthalmol.*, 91:873-877 (2007).
Lama et al., "Antifibrotics and wound healing in glaucoma surgery," *Surv. Ophthalmol.*, 48:314-346 (2003).
Lee et al., "Treatment of failing glaucoma filtering cystic blebs with tissue plasminogen activator (tPA)," *J. Ocul. Pharmacol. Ther.*, 11:227-232 (1995).
Mali et al., "Plasminogen activators promote excitotoxicity-induced retinal damage," *FASEB J.*, 19:1280-1289 (2005).
Matsumoto et al., "Normal tension glaucoma and primary open angle glaucoma associated with increased platelet aggregation," *Tohoku J. Exp. Med.*, 193:293-299 (2001).
Miller et al.., "An animal model of filtration surgery," *Trans. Ophthalmol. Soc. UK*, 104:893-897 (1985).
No Author Listed, "Comparison of glaucomatous progression between untreated patients with normal-tension glaucoma and patients with therapeutically reduced intraocular pressures. Collaborative Normal-Tension Glaucoma Study Group," *Am. J. Ophthalmol.*, 126:487-497 (1998).
Novokhatny et al., "Thrombolytic potential of locally delivered active plasmin (Pm): in vitro assessment and in vivo comparison with tPA in the rabbit jugular vein thrombosis model," *Blood*, 97b:Abstract 3400 (1998).
Powell et al., "Activation of human neo-plasminogen-Val$_{442}$ by urokinase and streptokinase and a kinetic characterization of neoplasmin-Val$_{442}$," *J. Biol. Chem.*, 255:5329-5335 (1980).
Quigley, "Number of people with glaucoma worldwide," *Br. J. Ophthalmol.*, 80:389-393 (1996).
Robbins et al., "Human plasminogen and plasmin," *Methods Enzymol.*, 19:184-199 (1970).
Ruyssen et al., Chapter IX—Plasmin, In "Pharmaceutical Enzymes," Story-Scientia, Gent, Belgium, 123-131 (1978).
Salonen et al., "Rapid appearance of plasmin in tear fluid after ocular allergen exposure," *Clin. Exp. Immunol.*, 73(1):146-148 (1988).
Skuta et al., "Wound healing in glaucoma filtering surgery," *Surv. Ophthalmol.*, 32:149-170 (1987).
Smith et al., "Use of tissue plasminogen activator to revive blebs following intraocular surgery," *Arch Ophthalmol.*, 119:809-812 (2001).
Wang et al., "Structure and function of microplasminogen: I. Methionine shuffling, chemical proteolysis, and proenzyme activation," *Protein Sci.*, 4:1758-1767 (1995).
Wimmer et al., "Plasminogen activator inhibitor (PAI)-1 in the aqueous humor of glaucoma and the correlation to bleb scarring after trabeculectomy," *Invest. Ophthalmol. Vis. Sci.*, 45:E-Abstract 975 (2004).
International Search Report for App. Ser. No. PCT/EP2010/062584, mailed Nov. 17, 2010, 5 pages.
International Preliminary Report on Patentability and Written Opinion for App. Ser. No. PCT/EP2010/062584, dated Feb. 28, 2012, 6 pages.
Collaborative Normal-Tension Glaucoma Study Group, "Comparison of glaucomatous progression between untreated patients with normal-tension glaucoma and patients with therapeutically reduced intraocular pressures," *Am J Opthalmol.*, 126:487-497 (1998).

(56) References Cited

OTHER PUBLICATIONS

Li et al., "Inhibition of vascular endothelial growth factor reduces scar formation after glaucoma filtration surgery," *Invest Ophthalmol Vis Sci.*, 50:5217-5225 (2009).

Li et al., "Role of vascular endothelial growth factor and placental growth factor in glaucoma and scar formation after glaucoma filtration surgery," Free papers glaucoma: microbiology and bloodflow and IOP (2006).

Stalmans et al., "Enzymatic vitreolysis with ocriplasmin for vitreomacular traction and macular holes," *N Engl J Med.*, 367:606-615 (2012).

Van Bergen et al., "Role of placental growth factor (PLGF) in wound healing after glaucoma filtration surgery," *Bull Soc Belge Ophtalmol.*, 317:65-66 (2011).

Van Bergen et al., "The role of different VEGF isoforms in scar formation after glaucoma filtration surgery," *Exp Eye Res.*, 93:689-699 (2011).

Fourman et al., "Effects of tissue plasminogen activator on glaucoma filter blebs in rabbits," *Ophthalmic Surg.*, 20(9):663-667 (1989).

Mehra et al., "Fibrinolytic activity in blood and aqueous humour in glaucoma," *Indian J Ophthalmol.*, 31:827-829 (1983).

Olivier et al., "Intracameral tissue plasminogen activator in neovascular glaucoma," *Arch Ophthalmol.*, 111:586 (1993).

Ortiz et al., "Filtering bleb thrombolysis with tissue plasminogen activator," *Am J Ophthalmol.*, 106:624-625 (1988).

Ozment et al., "The use of tissue plasminogen activator in experimental filtration surgery," *Ophthalmic Surg.*, 23:22-30 (1992).

Piltz et al., "The use of subconjunctivally administered tissue plasminogen activator after trabeculectomy," *Ophthalmic Surg.*, 25:51-53 (1994).

Tripathi et al., "Intracameral tissue plasminogen activator for resolution of fibrin clots after glaucoma filtering procedures," *Am J Ophthalmol.*, 111:247-248 (1991).

\* cited by examiner

```
1          11         21         31         41         51
|          |          |          |          |          |
EPLDDYVNTQ GASLFSVTKK QLGAGSIEEC AAKCEEDEEF TCRAFQYHSK EQQCVIMAEN
61         71         81         91         101        111
|          |          |          |          |          |
RKSSIIIRMR DVVLFEKKVY LSECKTGNGK NYRGTMSKTK NGITCQKWSS TSPHRPRFSP
121        131        141        151        161        171
|          |          |          |          |          |
ATHPSEGLEE NYCRNPDNDP QGPWCYTTDP EKRYDYCDIL ECEEECMHCS GENYDGKISK
181        191        201        211        221        231
|          |          |          |          |          |
TMSGLECQAW DSQSPHAHGY IPSKFPNKNL KKNYCRNPDR ELRPWCFTTD PNKRWELCDI
241        251        261        271        281        291
|          |          |          |          |          |
PRCTTPPPSS GETYQCLKGT GENYRGNVAV TVSGHTCQHW SAQTPHTHNR TPENFPCKNL
301        311        321        331        341        351
|          |          |          |          |          |
DENYCRNPDG KRAPWCHTTN SQVRWEYCKI PSCDSSPVST EQLAPTAPPE LTPVVQDCYH
361        371        381        391        401        411
|          |          |          |          |          |
GDGQSYRGTS STTTTGKKCQ SWSSMTPHRH QKTPENYPNA GLTMNYCRNP DADKGPWCFT
421        431        441        451        461        471
|          |          |          |          |          |
TDPSVRWEYC NLKKCSGTEA SVVAPPPVVL LPDVETPSEE DCMFGNGKGY RGKRATTVTG
481        491        501        511        521        531
|          |          |          |          |          |
TPCQDWAAQE PHRHSIFTPE TNPRAGLEKN YCRNPDGDVG GPWCYTTNPR KLYDYCDVPQ
541        551        561        571        581        591
|          |          |1         9|         19|        29|        39
|          |          ||          |          |          |          |
CAAPSFDCGK PQVEPKKCPG RVVGGCVAHP HSWPWQVSLR TRFGMHFCGG TLISPEWVLT
601        611        621        631        641        651
|          49|        59|        69|        79|        89|        99
|          ||         ||         ||         ||         ||         |
AAHCLEKSPR PSSYKVILGA HQEVNLEPHV QEIEVSRLFL EPTRKDIALL KLSSPAVITD
661        671        681        691        701        711
|          109|       119|       129|       139|       149|       159
|          ||         ||         ||         ||         ||         |
KVIPACLPSP NYVVADRTEC FITGWGETQG TFGAGLLKEA QLPVIENKVC NRYEFLNGRV
721        731        741        751        761        771
|          169|       179|       189|       199|       209|       219
|          ||         ||         ||         ||         ||         |
QSTELCAGHL AGGTDSCQGD SGGPLVCFEK DKYILQGVTS WGLGCARPNK PGVYVRVSRF
781        791
|          229|
|          ||
VTWIEGVMRN N (SEQ ID NO:1)
```

FIGURE 1

PRIOR ART

SEQUENCE LISTING

<160> NUMBER OF SEQ ID NOS: 1

<210> SEQ ID NO 1
<211> LENGTH: 791
<212> TYPE: PRT
<213> ORGANISM: Homo sapiens

<400> SEQUENCE: 1

```
Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95
```

```
Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
            115                 120                 125

Glu Glu Asn Tyr Cys Arg Asn Pro Asp Asn Pro Gln Gly Pro Trp
            130                 135                 140

Cys Tyr Thr Thr Asp Pro Glu Lys Arg Tyr Asp Tyr Cys Asp Ile Leu
145                 150                 155                 160

Glu Cys Glu Glu Glu Cys Met His Cys Ser Gly Glu Asn Tyr Asp Gly
                165                 170                 175

Lys Ile Ser Lys Thr Met Ser Gly Leu Glu Cys Gln Ala Trp Asp Ser
            180                 185                 190

Gln Ser Pro His Ala His Gly Tyr Ile Pro Ser Lys Phe Pro Asn Lys
            195                 200                 205

Asn Leu Lys Lys Asn Tyr Cys Arg Asn Pro Asp Arg Glu Leu Arg Pro
            210                 215                 220

Trp Cys Phe Thr Thr Asp Pro Asn Lys Arg Trp Glu Leu Cys Asp Ile
225                 230                 235                 240

Pro Arg Cys Thr Thr Pro Pro Ser Ser Gly Pro Thr Tyr Gln Cys
            245                 250                 255

Leu Lys Gly Thr Gly Glu Asn Tyr Arg Gly Asn Val Ala Val Thr Val
            260                 265                 270

Ser Gly His Thr Cys Gln His Trp Ser Ala Gln Thr Pro His Thr His
            275                 280                 285

Asn Arg Thr Pro Glu Asn Phe Pro Cys Lys Asn Leu Asp Glu Asn Tyr
            290                 295                 300

Cys Arg Asn Pro Asp Gly Lys Arg Ala Pro Trp Cys His Thr Thr Asn
305                 310                 315                 320

Ser Gln Val Arg Trp Glu Tyr Cys Lys Ile Pro Ser Cys Asp Ser Ser
            325                 330                 335

Pro Val Ser Thr Glu Gln Leu Ala Pro Thr Ala Pro Pro Glu Leu Thr
            340                 345                 350

Pro Val Val Gln Asp Cys Tyr His Gly Asp Gly Gln Ser Tyr Arg Gly
            355                 360                 365

Thr Ser Ser Thr Thr Thr Thr Gly Lys Lys Cys Gln Ser Trp Ser Ser
            370                 375                 380

Met Thr Pro His Arg His Gln Lys Thr Pro Glu Asn Tyr Pro Asn Ala
385                 390                 395                 400

Gly Leu Thr Met Asn Tyr Cys Arg Asn Pro Asp Ala Asp Lys Gly Pro
                405                 410                 415

Trp Cys Phe Thr Thr Asp Pro Ser Val Arg Trp Glu Tyr Cys Asn Leu
            420                 425                 430

Lys Lys Cys Ser Gly Thr Glu Ala Ser Val Val Ala Pro Pro Pro Val
            435                 440                 445

Val Leu Leu Pro Asp Val Glu Thr Pro Ser Glu Glu Asp Cys Met Phe
            450                 455                 460

Gly Asn Gly Lys Gly Tyr Arg Gly Lys Arg Ala Thr Thr Val Thr Gly
465                 470                 475                 480

Thr Pro Cys Gln Asp Trp Ala Ala Gln Glu Pro His Arg His Ser Ile
                485                 490                 495

Phe Thr Pro Glu Thr Asn Pro Arg Ala Gly Leu Glu Lys Asn Tyr Cys
            500                 505                 510
```

-continued

```
Arg Asn Pro Asp Gly Asp Val Gly Gly Pro Trp Cys Tyr Thr Thr Asn
    515                 520                 525
Pro Arg Lys Leu Tyr Asp Tyr Cys Asp Val Pro Gln Cys Ala Ala Pro
    530                 535                 540
Ser Phe Asp Cys Gly Lys Pro Gln Val Glu Pro Lys Lys Cys Pro Gly
545                 550                 555                 560
Arg Val Val Gly Gly Cys Val Ala His Pro His Ser Trp Pro Trp Gln
                565                 570                 575
Val Ser Leu Arg Thr Arg Phe Gly Met His Phe Cys Gly Gly Thr Leu
            580                 585                 590
Ile Ser Pro Glu Trp Val Leu Thr Ala Ala His Cys Leu Glu Lys Ser
        595                 600                 605
Pro Arg Pro Ser Ser Tyr Lys Val Ile Leu Gly Ala His Gln Glu Val
    610                 615                 620
Asn Leu Glu Pro His Val Gln Glu Ile Glu Val Ser Arg Leu Phe Leu
625                 630                 635                 640
Glu Pro Thr Arg Lys Asp Ile Ala Leu Leu Lys Leu Ser Ser Pro Ala
                645                 650                 655
Val Ile Thr Asp Lys Val Ile Pro Ala Cys Leu Pro Ser Pro Asn Tyr
            660                 665                 670
Val Val Ala Asp Arg Thr Glu Cys Phe Ile Thr Gly Trp Gly Glu Thr
        675                 680                 685
Gln Gly Thr Phe Gly Ala Gly Leu Leu Lys Glu Ala Gln Leu Pro Val
    690                 695                 700
Ile Glu Asn Lys Val Cys Asn Arg Tyr Glu Phe Leu Asn Gly Arg Val
705                 710                 715                 720
Gln Ser Thr Glu Leu Cys Ala Gly His Leu Ala Gly Gly Thr Asp Ser
                725                 730                 735
Cys Gln Gly Asp Ser Gly Gly Pro Leu Val Cys Phe Glu Lys Asp Lys
            740                 745                 750
Tyr Ile Leu Gln Gly Val Thr Ser Trp Gly Leu Gly Cys Ala Arg Pro
        755                 760                 765
Asn Lys Pro Gly Val Tyr Val Arg Val Ser Arg Phe Val Thr Trp Ile
    770                 775                 780
Glu Gly Val Met Arg Asn Asn
785                 790
```

METHOD FOR TREATING FILTRATION FAILURE AFTER TRABECULECTOMY SURGERY

CROSSREFERENCE TO RELATED APPLICATIONS

This application is a continuation of U.S. application Ser. No. 13/392,623, filed Mar. 19, 2012, now abandoned, which is a 371 of PCT/EP2010/062584, filed Aug. 27, 2010, which claims the benefit of U.S. Provisional Appl. No. 61/237,723 filed Aug. 28, 2009 and EP 09168912.5, filed Aug. 28, 2009.

FIELD OF THE INVENTION

The current invention relates to the improvement of trabeculectomy surgery. The improvement more specifically resides in an extended lifetime of the sclera-corneal drainage channel created by trabeculectomy surgery. The improvement is obtained by post-surgical administration of a plasmin or active derivative thereof in the form of topical eye drops alone, by anterior chamber injection alone, or by any combination of these.

BACKGROUND OF THE INVENTION

Glaucoma is a multifactorial, neurodegenerative disease and the second most important cause of irreversible blindness (Quigley, 1996, Br J Ophthalmol 80, 389-393). This disease is characterized by progressive retinal ganglion cell apoptosis, resulting in visual field loss. Current treatment of this disease is directed towards the reduction of intraocular pressure (IOP), which is the main risk factor for glaucoma (Collaborative Normal-Tension Glaucoma Study Group, 1998, Am J Opthalmol 126, 487-497).

Of all currently used treatments to lower IOP, filtration surgery (trabeculectomy) was shown to be the most effective (Burr et al., 2005, Cochrane Database Syst Rev 18(2): CD004399; Hitchings, 1998, Arch Ophthalmol 116, 241-242). A trabeculectomy creates a "controlled" leak of fluid (aqueous humor) from the eye, which percolates under the conjunctiva. During the operation a piece of trabecular meshwork in the drainage angle of the eye is removed, creating an opening. The opening is partially covered with a flap of tissue from the sclera and conjunctiva. A small conjunctival "bleb" (bubble) appears at the junction of the cornea and the sclera (limbus) where this surgically produced valve is made.

In 30% of the cases, however, the constructed channel closes due to excessive scar tissue formation, resulting in surgical failure (Addicks et al., 1983, Arch Ophthalmol 101, 795-798). The 4 important processes contributing to post-operative conjunctival scarring are: clot formation, inflammation, angiogenesis and fibrosis (Lee et al., 1995, J Ocul Pharmacol Ther 11, 227-232; Lama & Fechtner, 2003, Surv Ophthalmol 48, 314-346). Indeed, increased conjunctival infiltration of inflammatory cells and Tenon fibroblasts (Hitchings & Grierson, 1983, Trans Ophthalmol Soc UK 103, 84-88; Skuta & Parrish, 1987, Surv Ophthalmol 32, 149-170), and higher levels of bleb vascularization (Jampel et al., 1988, Arch Ophthalmol 106, 89-94) are associated with surgical failure. These processes are mediated by various cytokines (e.g. IL-1 and INF-α2b) and growth factors (e.g. PDGF, FGF, TGF-β1 and VEGF (Lama & Fechtner, 2003; Gillies & Su, 1991, Aust NZ J Ophthalmol 19, 299-304)). Preoperative anti-mitotics, such as mitomycin-C and 5-Fluorouracyl can improve surgical outcome (Quigley, 1996; Katz et al., 1995, Ophthalmol 102, 1263-1269). However, these antimetabolites carry a risk of vision-threatening complications such as scleral thinning and infections (Lama & Fechtner, 2003; Hitchings & Grierson, 1983; Skuta & Parrish, 1987; Jampel et al., 1988; Gillies & Su, 1991; Katz et al., 1995; Greenfield et al., 1998, Arch Ophthalmol 116, 443-447). Furthermore, blocking TGF-β seemed promising in animal models (Cordeiro et al., 2003, Gene Ther 10, 59-71), but was not efficient in a clinical study (CAT-152 0102 Trabeculectomy Study Group, Kwah, Grehn, 2007, Ophthalmol 114, 1822-1830). The number of post-trabeculectomy interventions expressed as the incidence of post-surgery "bleb manipulations" was reported to be as high as 78% (King et al., 2007, Br J Ophthalmol 91, 873-877). Therefore, there is still a need for alternative strategies to prevent filtration failure and, thus, to reduce the incidence of bleb manipulations.

Microplasmin is a recombinant protein that dissolves blood clots by degrading fibrin. Recently, microplasmin has been shown to be efficient, well tolerated and safe for intraocular use in a phase II clinical trial to study its efficacy to induce non-surgical posterior vitreous detachment, PVD (Gandorfer, 2008, Eye 22, 1273-1277; WO 2004/052228) and is currently under investigation in phase III clinical trials. Plasmin was previously shown to be able to induce PVD as well (e.g. U.S. Pat. No. 5,304,118). The mechanism by which PVD is induced by plasmin or microplasmin is currently not fully understood. Unsupported by any or any conclusive experimental data, WO 2009/073457 and WO 2009/067407 propose subconjunctival plasmin injection for rescuing filtering blebs and the use of matrix metalloproteinase activating proteases for reducing IOP, respectively.

SUMMARY OF THE INVENTION

The invention relates to (the use of) a plasmin or an active truncated variant thereof (for the manufacture of a medicament) for treating filtration failure after trabeculectomy surgery of an eye, or for preventing, reducing or retarding the occurrence of filtration failure after trabeculectomy surgery of an eye.

Said plasmin or active truncated variant thereof, or said medicament, may be in a pharmaceutically acceptable formulation capable of being administered to an eye as topical eye drops. Alternatively, said plasmin or active truncated variant thereof, or said medicament, may be a in pharmaceutically acceptable formulation capable of being administered by injection into the anterior chamber of an eye.

The treatment of filtration failure after trabeculectomy surgery of an eye, or the prevention, reduction or retardation of the occurrence of filtration failure after trabeculectomy surgery of an eye may result from contacting said eye with an effective amount of topical eye drops comprising said plasmin or active truncated variant thereof. Alternatively, it may result from introduction into the anterior chamber of an eye of an effective amount of said plasmin or active truncated variant thereof. In a further alternative, it may result from contacting said eye with an effective amount of topical eye drops comprising said plasmin or active truncated variant thereof, combined with introduction into the anterior chamber of an eye of an effective amount of said plasmin or active truncated variant thereof.

In any of the above, said active truncated variant of plasmin may be lacking one or more kringle domains and/or lacking parts of one or more kringle domains. More specifically, said active truncated variant of plasmin may be selected from the group consisting of midiplasmin, miniplasmin, microplasmin or deltaplasmin.

The invention further covers the (use of) a plasmin or an active truncated variant thereof (for the manufacture of a medicament) for treating filtration failure after trabeculectomy surgery of an eye, or for preventing, reducing or retarding the occurrence of filtration failure after trabeculectomy surgery of an eye, wherein said plasmin or active truncated variant thereof, or said medicament, may be in a pharmaceutically acceptable formulation further comprising one or more of an agent for controlling the intra-ocular pressure, an anti-inflammatory agent, an antiviral agent, an antibacterial agent, an antiviral agent, an anti-angiogenic agent, an anti-mitotic agent, an antihistamine, an anesthetic, an agent to induce mydriasis and an agent to induce cycloplegia. Alternatively, when said further agent(s) is(are) not included in the pharmaceutically acceptable formulation, or in the medicament, said eye may be contacted further with one or more agents chosen from an agent for controlling the intra-ocular pressure, an anti-inflammatory agent, an antiviral agent, an antibacterial agent, an antiviral agent, an anti-angiogenic agent, an anti-mitotic agent, an antihistamine, an anesthetic, an agent to induce mydriasis and an agent to induce cycloplegia.

LEGENDS TO THE FIGURES

FIG. 1 shows the amino acid sequence with double numbering of the amino acid positions of wild-type human Glu-plasminogen (1 to 791) and of the plasmin catalytic domain (1 to 230, amino acid sequence and numbering in bold). Microplasminogen as used for demonstrating the invention starts at amino acid position 543 (numbering relative to Glu-plasminogen). Kringle domains (as derived from GenBank accession number AAA36451) are boxed and their amino acid sequences typed alternating in normal and italic letters. The catalytic triad amino acids are circled.

FIG. 2 schematically depicts an eye after trabeculectomy. The arrow shaded with vertical lines indicates the flow of aqueous liquid from the eye's anterior chamber to the outside through the filtration channel created by trabeculectomy.

Figure 3:
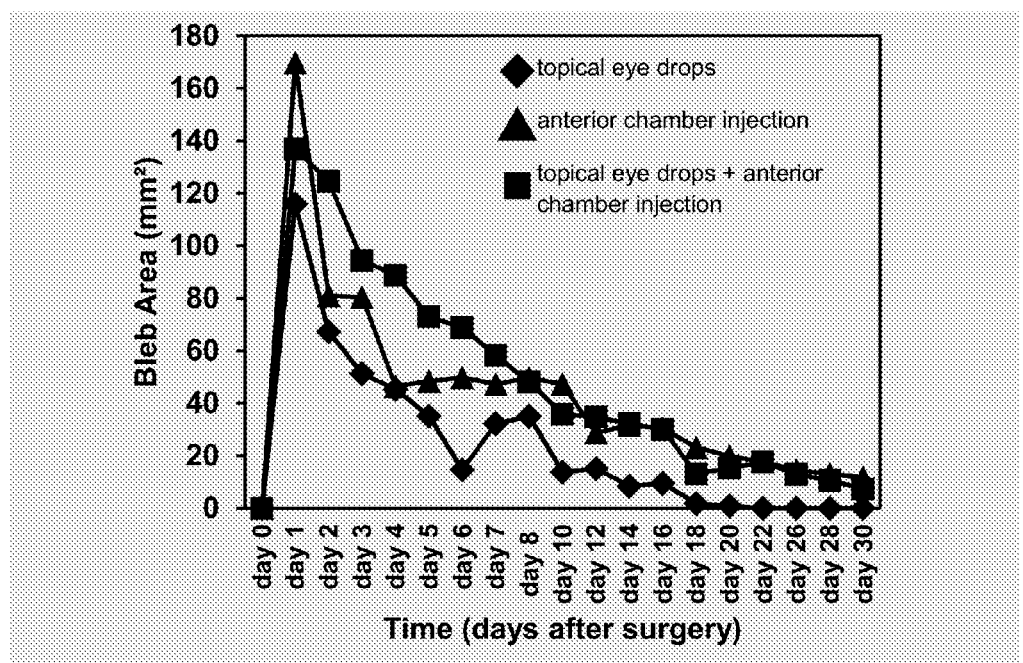

FIG. 3 depicts the results obtained after trabeculectomy combined with (i) post-operative administration of topical drops containing microplasmin (diamonds), (ii) post-operative anterior chamber injection of microplasmin (triangles), or (iii) combined post-operative administration of topical drops containing microplasmin and anterior chamber injection of microplasmin (squares). The data are normalized meaning that background values obtained with placebo treatment have been deducted from the values obtained with non-placebo treatment.

DETAILED DESCRIPTION OF THE INVENTION

The present invention is based on the effect of administration of microplasmin on the clinical outcome of trabeculectomy surgery, said effect being positive and resulting in the prevention, reduction or retardation of the occurrence of filtration failure. As known from clinical practice, each patient that underwent trabeculectomy surgery is at significant risk to develop filtration failure.

Therefore, the invention relates to (the use of) a plasmin or an active truncated variant thereof (for the manufacture of a medicament) for treating filtration failure after trabeculectomy surgery of an eye, or for preventing, reducing or retarding the occurrence of filtration failure after trabeculectomy surgery of an eye.

"Plasmin", also known as fibrinolysin or lysofibrin, is a serine-type protease which results from the activation of the zymogen plasminogen. Activation is the result of a proteolytic cleavage between amino acids 561 and 562 (numbering relative to human Glu-plasminogen). Plasmin carries a heavy chain comprising 5 kringle domains and a light chain comprising the catalytic domain. Plasminogen can be enriched from blood plasma, e.g., via lysine affinity-chromatography (Deutsch & Mertz, 1970, Science 170, 1095-1096). Truncation of the plasmin molecule is possible as long as the catalytic domain remains functional, such truncation thus results in the formation of an "active truncated variant" of plasmin. As such, one or more of the 5 kringle domains can be deleted wholly or partially. Truncated plasmins lacking one or more kringle domains and/or lacking parts of one or more kringle domains therefore are envisaged by the current invention. Examples of truncated variants of plasmin include, but are not limited to, "midiplasmin", "miniplasmin", "microplasmin", and "delta-plasmin". Midiplasmin is basically lacking kringle domains 1 to 3 (e.g. Christensen et al., 1995, Biochem J 305, 97-102). Miniplasmin was originally obtained by limited digestion of plasmin with elastase and is basically lacking kringle domains 1 to 4 (e.g. Christensen et al., 1979, Biochim Biophys Acta 567, 472-481; Powell & Castellino, 1980, J Biol Chem 255, 5329). Miniplasmin has subsequently been produced recombinantly (WO 2002/050290). Microplasmin was originally obtained by incubation of plasmin at elevated pH and is basically lacking all kringle domains (e.g. WO 89/01336). Whereas the microplasmin obtained from incubation of plasmin at elevated pH is containing the 30-31 carboxy-terminal amino acids of the heavy chain, a recombinantly produced microplasmin variant contains the 19 carboxy-terminal amino acids of the heavy chain (WO 2002/050290). Delta-plasmin is a recombinant version of plasmin in which kringle domain 1 is linked directly with the catalytic domain (WO 2005/105990). The above described truncated variants of plasmin are obtained by activation of "midiplasminogen", "miniplasminogen", "microplasminogen" and "delta-plasminogen", respectively. In order to be activatable, a truncated plasminogen needs to comprise a minimum number of amino acids of the linker between the kringle 5 domain and the catalytic domain (see, e.g., Wang et al., 1995, Protein Science 4, 1758-1767). As alternative to plasmin or an active truncated variant thereof, an activatable plasminogen or an activatable truncated variant thereof can be used in the context of the current invention (see, e.g. EP 0480906; U.S. Pat. No. 5,304,383; EP 0631786; U.S. Pat. No. 5,520,912; U.S. Pat. No. 5,597,800; U.S. Pat. No. 5,776,452). "Plasminogen" refers to any form of plasminogen e.g. Glu-plasminogen or Lys-plasminogen (starting with Arg at position 68 or Lys at positions 77 or 78). When using activatable plasminogen or an activatable truncated variant thereof, the activation to plasmin may be delayed and will occur after contacting it with an organ, tissue or body fluid. In yet another alternative, the plasmin or an active truncated variant thereof can be substituted in the context of the current invention for an activatable plasminogen or an activatable truncated variant thereof in conjunction with a plasminogen activator (such as tissue plasminogen activator (tPA), urokinase, streptokinase or staphylokinase; see, e.g. U.S. Pat. No. 6,733,750; U.S. Pat. No. 6,585,972; U.S. Pat. No. 6,899,877; WO 03/33019). In yet a further alternative, a mixture of any of (i) plasmin or an active truncated variant thereof, (ii) activatable plasminogen or an activatable truncated variant thereof, and (iii) a plasminogen activator can be used in the context of the current invention (see, e.g. US 2004/0081643). In order to ensure stability of the plasmin (or plasminogen), it will generally be stored at lowered temperatures (e.g. 4 degrees Celsius or −20 degrees Celsius) in a stabilizing composition such as low pH (pH 4 or lower; obtained by e.g. 1 mM to 250 mM of an acid such as citric acid, see, e.g. Castellino & Sodetz, 1976, Methods Enzymol 45, 273-286; WO 01/36608; WO 01/36609; WO 01/36611) or high glycerol content (30-50% v/v, e.g., Castellino & Sodetz, 1976, Methods Enzymol 45, 273-286), alternatively in or in conjunction with one or more further stabilizers such as an amino acid (e.g. lysine or an analogue thereof), a sugar (e.g. mannitol) or any stabilizer as known in the art (e.g. dipeptides, WO 97/01631). Further included in the genus "plasmin" is any active derivative thereof (or of an active truncated plasmin variant), or similar derivative of activatable plasminogen (or of activatable truncated variant thereof). Such derivates include e.g. labeled plasmin or plasminogen (or truncated variants thereof) such as $Tc^{99}$-labeled plasmin (Deacon et al., 1980, Br J Radiol 53, 673-677) or pegylated or acylated plasmin or plasminogen (or truncated variants thereof; EP 9879, WO 93/15189). Said derivatives further include hybrid or chimeric plasmin or plasminogen molecules comprising e.g. a truncated plasmin or plasminogen according to the invention fused with e.g. a fibrin-binding molecule (such as kringle 2 of tPA, an apolipoprotein kringle, the finger domain of tPA or fibronectin and the Fab domain of a fibrin-binding antibody).

Many assays exist to determine whether or not a plasmin species is proteolytically active. Easy and straightforward assays are based on the digestion of a chromogenic substrate by plasmin present in a sample; chromogenic substrates include S-2403 and S-2251 which release p-nitroaniline (pNA) upon proteolytic cleavage. The amount of pNA formed can be measured by light absorbance at 405 nm. An alternative assay for determining plasmin activity is a potentiometric assay. Colorimetric (using a chromogenic substrate) and potentiometric assays are described in e.g., Castellino & Sodetz (1976, Methods Enzymol 45, 273-286). A further alternative assay for determining plasmin activity is a caseinolytic assay (e.g., Robbins & Summaria, 1970, Methods Enzymol 19, 184-199; Ruyssen & Lauwers, 1978, Chapter IX—Plasmin, In "Pharmaceutical Enzymes", Story-Scientia, Gent, Belgium, pp. 123-131). Yet another alternative assay for determining plasmin activity is a fibrinolytic assay (e.g., Astrup & Mullertz, 1952, Arch Biochem Biophys 40, 346-351). Any suitably labeled natural substrate of plasmin can in fact be used by the skilled person to design a plasmin activity assay.

The "trabecular meshwork (TM)" is a mesh-like structure inside the eye at the iris-scleral junction of the anterior chamber angle. The TM filters the aqueous fluid and controls its flow into the canal of Schlemm prior to its leaving the anterior chamber. Increased resistance in the TM leads to reduced aqueous fluid outflow and thus increased intra-ocular pressure (IOP).

When left untreated, this elevated IOP leads to glaucomatous damage to the optic nerve and retinal nerve fibers, and leads to loss of vision. This vision loss can be prevented or halted by administering medication, an "agent for controlling the intra-ocular pressure", which controls the intra-ocular pressure. Such medicaments include adrenergic blocking agents (beta blockers or sympatholytic drugs such as betaxolol, carteolol, levobunolol, metipanolol and timolol), adrenergic stimulating agents (sympathomimetic drugs such as aproclonidine, epinephrine, hydroxyamphetamine, phenylephrine, naphazoline and tetrahydrozaline), carbonic anhydrase inhibitors (such as systemic acetozolamide, and topical brinzolamide and dorzolamide), miotics (cholinergic stimulating agents, parasympathomimetic drugs such as carbachol and pilocarpine), osmotic agents (such as glycerin and mannitol), prostaglandin and prostaglandin analogues (prostamides, bimatoprost, unoprostone isopropyl, travoprost, latanoprost, natural prostaglandin, prostaglandin F2α, and FP prostanoid receptor agonists). When such medicaments are not efficient (or not anymore), then filtration surgery is a viable treatment.

"Trabeculectomy", "trabeculectomy surgery" or "filtration surgery", is defined as a surgical procedure on the eye wherein part of the trabecular meshwork is removed whereby a filtration site (a sclera-corneal drainage channel) is created that increases the outflow of aqueous fluid from the eye; this type of filtering procedure is commonly used in the treatment of glaucoma, and more specifically to reduce the IOP in an eye subject to/suffering from glaucoma. FIG. 2 is a schematic representation of the result of trabeculectomy surgery.

"Filtration failure" is a condition reversing the clinically desired effect of trabeculectomy surgery, i.e., reversing the desired drop in IOP. The initial post-operative time is crucial in the sense that eye-healing activities are highest in this period. This period of high eye-healing capacity is dependent upon the species and spans about 2 weeks for rabbits and up to 1- to 2-months in humans. Upon contacting plasmin or an active truncated variant thereof (or any alternative therefore as described above) with an eye according to the current invention, the frequency of occurrence of filtration failure over a given period of time is lowered. Plasmin or an active truncated variant thereof (or any alternative therefore as described above) used according to the current invention thus results in the prevention, reduction or retarding of the occurrence of filtration failure.

The plasmin or active truncated variant thereof of the invention, or the medicament containing one or more of them, for treating filtration failure after trabeculectomy surgery of an eye, or for preventing, reducing or retarding the occurrence of filtration failure after trabeculectomy surgery of an eye may be in a pharmaceutically acceptable formulation capable of being administered to an eye as topical eye drops. Alternatively, the plasmin or active truncated variant thereof of the invention, or the medicament containing one or more of them, is in a pharmaceutically acceptable formulation capable of being administered by injection into the anterior chamber of an eye. The composition of the eye drop formulation and the formulation for injection into the anterior chamber of an eye may be the same or different. To obtain optimal clinical outcomes, the compositions of the formulations may need to be adjusted to their mode of application and may thus need to be different.

The treatment of filtration failure after trabeculectomy surgery of an eye, or the prevention, reduction or retardation of the occurrence of filtration failure after trabeculectomy surgery of an eye may result from contacting said eye with an effective amount of topical eye drops comprising said plasmin or active truncated variant thereof. In other words, for treatment of filtration failure after trabeculectomy surgery of an eye, or for prevention, reduction or retardation of the occurrence of filtration failure after trabeculectomy surgery of an eye, the effective amount of plasmin or active truncated variant thereof may be or is to be administered in the form of topical eye drops.

Alternatively, the treatment of filtration failure after trabeculectomy surgery of an eye, or the prevention, reduction or retardation of the occurrence of filtration failure after trabeculectomy surgery of an eye may result from introduction into the anterior chamber of an eye of an effective amount of said plasmin or active truncated variant thereof. In other words, for treatment of filtration failure after trabeculectomy surgery of an eye, or for prevention, reduction or retardation of the occurrence of filtration failure after trabeculectomy surgery of an eye, the effective amount of plasmin or active truncated variant thereof may be or is to be administered by introduction or injection into the anterior chamber of an eye.

In a further alternative, the treatment of filtration failure after trabeculectomy surgery of an eye, or the prevention, reduction or retardation of the occurrence of filtration failure after trabeculectomy surgery of an eye may result from contacting said eye with an effective amount of topical eye drops comprising said plasmin or active truncated variant thereof, combined with introduction into the anterior chamber of an eye of an effective amount of said plasmin or active truncated variant thereof. The effective amount of plasmin or active truncated variant thereof may in this case be reached only by the combined administrations. In other words, for treatment of filtration failure after trabeculectomy surgery of an eye, or for prevention, reduction or retardation of the occurrence of filtration failure after trabeculectomy surgery of an eye, the effective amount of plasmin or active truncated variant thereof is to be administered in the form of topical eye drops combined with introduction or injection into the anterior chamber of an eye. In the above, the amount or concentration of active substance in the eye drop formulation and in the formulation for anterior chamber intracameral injection may be the same or different. The amounts or concentrations of active substance may need to be adjusted such as to the mode of application or such as to minimize eventual side effects that may occur when e.g. administering a high amount or concentration of active substance by either one of the administration routes. In the latter case, the effective amount of active substance can still be reached by compensation of a low amount or concentration of active substance via one administration route by a higher amount or concentration of active substance via the other administration route.

In an embodiment to any of the above, said active truncated variant of plasmin may be lacking one or more kringle domains and/or lacking parts of one or more kringle domains. More specifically, said active truncated variant of plasmin may be selected from the group consisting of midiplasmin, miniplasmin, microplasmin or deltaplasmin.

The invention further covers the (use of) a plasmin or an active truncated variant thereof (for the manufacture of a medicament) for treating filtration failure after trabeculectomy surgery of an eye, or for preventing, reducing or retarding the occurrence of filtration failure after trabeculectomy surgery of an eye, which is in a pharmaceutically acceptable solution that may further comprise one or more of an agent for controlling the intra-ocular pressure, an anti-inflammatory agent, an antiviral agent, an antibacterial agent, an antiviral agent, an anti-angiogenic agent, an anti-mitotic agent, an antihistamine, an anesthetic, an agent to induce mydriasis and an agent to induce cycloplegia. Alternatively, when said further agent(s) is(are) not included in the pharmaceutically acceptable solution or medicament containing said plasmin or an active truncated variant thereof, said eye may be contacted further with one or more agents chosen from an agent for controlling the intra-ocular pressure, an anti-inflammatory agent, an antiviral agent, an antibacterial agent, an antiviral agent, an anti-angiogenic agent, an anti-mitotic agent, an antihistamine, an anesthetic, an agent to induce mydriasis and an agent to induce cycloplegia.

Methods of treatment of filtration failure after trabeculectomy surgery of an eye, and in particular methods of preventing, reducing or retarding the occurrence of filtration failure after trabeculectomy surgery of an eye are also envisaged. These methods comprise the step of contacting said eye after trabeculectomy surgery with a medicament comprising plasmin or an active truncated variant thereof wherein said contacting results in said treatment of filtration failure, or in said preventing, reducing or retarding of the occurrence of filtration failure. Modalities of said medicament, plasmin or an active truncated variant thereof according to the invention, and contacting are as described above.

In any of the above-described medical uses and methods, the plasmin can be substituted for plasminogen, plasminogen activators or any possible combination (whether or not in the same formulation or as separate solutions or medicaments) of plasmin (or any active truncated variant thereof), plasminogen, plasminogen activators, etc. as described earlier in the definition of "plasmin".

"Contacting" means any mode of administration that results in interaction between a composition such as a medicament and an object (such as conjunctiva or subconjunctival tissue) with which said composition is contacted. The interaction between the composition and the object can occur starting immediately or nearly immediately with the administration of the composition, can occur over an extended time period (starting immediately or nearly immediately with the administration of the composition), or can be delayed relative to the time of administration of the composition. More specifically the "contacting" may result in delivering an effective amount of the medicament to the object.

The term "effective amount" refers to the dosing regimen of the medicament according to the invention, in particular of the active ingredient of the medicament according to the invention, i.e., plasmin or an active truncated variant thereof (or any alternative therefore as described above). The effective amount will generally depend on and will need adjustment to the mode of contacting or administration. The effective amount of the medicament, more particular its active ingredient, is the amount required to obtain the desired clinical outcome or therapeutic or prophylactic effect without causing significant or unnecessary toxic effects. To obtain or maintain the effective amount, the medicament may be administered as a single dose or in multiple doses. The effective amount may further vary depending on the severity of the condition that needs to be treated or the expected severity of the condition that needs to be prevented or treated; this may depend on the overall health and physical condition of the patient and usually the treating doctor's or physician's assessment will be required to establish what is the effective amount. The effective amount may further be obtained by a combination of different types of contacting or administration. In the context of the present invention the effective amount may more particularly be obtained by either one or more of administration of topical eye drops, administration by injection into the anterior chamber of an eye or administration by subconjunctival injection. A typical dose of a single administration of the medicament of the invention may comprise 10 µg to 1 mg of the active compound (i.e., a plasmin or an active truncated variant thereof, or any alternative thereto as described higher). Administration of the medicament of the invention by means of injection typically is kept to a minimum, i.e., the frequency of repeat injections is kept to a minimum. Administration of the medicament of the invention by means of topical eye drops can be done more frequently, e.g., once per hour, or e.g. 1 to 6 times a day. As the first weeks or months post-trabeculectomy (species dependent as described higher) are crucial in the sense that eye-healing activities are highest in this period, the duration of treatment with a medicament according to the present invention should be adjusted to this period. Initial dosage and administration frequency may thus be relatively high and may be gradually decreased when the risk of the occurrence of filtration failure is decreasing.

In general, the medicament or composition of the invention comprising a plasmin (or any variant or derivative thereof or alternative thereto) according to the invention may, depending on its ultimate use and mode of administration, comprise one or more further active ingredients such as an agent controlling the intra-ocular pressure (see higher), an anticoagulant, a thrombolytic agent, an anti-inflammatory agent, an antiviral agent, an antibacterial agent, an antifungal agent, an anti-angiogenic agent, an anti-mitotic agent, an antihistamine or anesthetic.

"Anticoagulants" include hirudins, heparins, coumarins, low-molecular weight heparin, thrombin inhibitors, platelet inhibitors, platelet aggregation inhibitors, coagulation factor inhibitors, anti-fibrin antibodies and factor VIII-inhibitors (such as those described in WO 01/04269 and WO 2005/016455).

"Thrombolytic agents" include urokinase, streptokinase, tissue-type plasminogen activator (tPA), urokinase-type plasminogen activator (uPA) and staphylokinase or any variant or derivative of any thereof such as APSAC (anisoylated plasminogen streptokinase activator complex), alteplase, reteplase, tenecteplase, and scuPA (single chain uPA).

"Anti-inflammatory agents" include steroids (e.g. prednisolone, methylprednisolone, cortisone, hydrocortisone, prednisone, triamcinolone, dexamethasone) and non-steroidal anti-inflammatory agents (NSAIDs; e.g. acetaminophen, ibuprofen, aspirin).

"Antiviral agents" include trifluridine, vidarabine, acyclovir, valacyclovir, famciclovir, and doxuridine.

"Antibacterial agents" or antibiotics include ampicillin, penicillin, tetracycline, oxytetracycline, framycetin, gatifloxacin, gentamicin, tobramycin, bacitracin, neomycin and polymyxin.

"Anti-mycotic/fungistatic/antifungal agents" include fluconazole, amphotericin, clotrimazole, econazole, itraconazole, miconazole, 5-fluorocytosine, ketoconazole and natamycin.

"Anti-angiogenic agents" include antibodies (or fragments thereof) such as anti-VEGF (vascular endothelial growth factor) or anti-P1GF (placental growth factor) antibodies and agents such as macugen (pegaptanib sodium), tryptophanyl-tRNA synthetase (TrpRS), anecortave acetate, combrestatin A4 prodrug, AdPEDF (adenovector capable of expressing pigment epithelium-derived factor), VEGF-trap, inhibitor of VEGF receptor-2, inhibitors of VEGF, P1GF or TGF-β, Sirolimus (rapamycin) and endostatin.

"Anti-mitotic agents" include mitomycin C and 5-fluorouracyl.

"Antihistamine" includes ketitofen fumarate and pheniramine maleate.

"Anesthetics" include benzocaine, butamben, dibucaine, lidocaine, oxybuprocaine, pramoxine, proparacaine, proxymetacaine, tetracaine and amethocaine.

Other adjunct agents or drugs that can be used in conjunction with the plasmin or active variant thereof (or any alternative thereto as described above) according to the invention include scopoloamine, atropine or tropicamide, to induce mydriasis (pupillary dilation) and/or cycloplegia (paralysis of the eye focusing muscle).

In addition to plasmin or active truncated variant thereof (or any of the alternatives therefor as described above), each of the above listed agents as well as antihistamine and anesthetics is to be considered as an "active ingredient".

A "pharmaceutically acceptable formulation" is, in the context of the current invention more particular an "ophthalmologically acceptable formulation". A formulation in general is a composition comprising a carrier, diluent or adjunvant compatible with the one or more active ingredients to be formulated, the whole formulation being compatible with the intended use in the intended tissue or organ, etc. Examples of pharmaceutically acceptable formulations as well as methods for making them can be found, e.g., in Remington's Pharmaceutical Sciences (e.g. $20^{th}$ Edition; Lippincott, Williams & Wilkins, 2000) or in any Pharmacopeia handbook (e.g. US-, European- or International Pharmacopeia).

"Topical eye drops" typically contains an active ingredient (such as plasmin or an active truncated variant thereof or any alternative thereto as described higher) or a combination of active ingredients in a saline solution, and optionally one or more lubricants.

"Lubricants" include propylene glycerol, glycerin, carboxymethylcellulose, hydroxypropylmethylcellulose, soy lecithin, polyvinyl alcohol, white petrolatum, mineral oil, povidone, carbopol 980, polysorbate 80, dextran 70.

EXAMPLES

The Examples included hereafter demonstrate the invention and are not construed to be limiting the scope of the invention in any way.

Example 1

Rabbit Model for Glaucoma Filtration Surgery

Female New-Zealand rabbits, aged 12 to 14 weeks and weighing 2 to 3 kg, underwent a filtration surgery (trabeculectomy) in both eyes in the same way as in human eyes, except that in rabbits a much more aggressive postoperative fibrosis occurs, resulting in a filtration failure after 10 to 14 days (Miller et al., 1985, Trans Ophthalmol Soc UK 104, 893-897).

General anesthesia was induced with an intramuscular injection of Ketalar (50 mg/ml) and Rompun (2%). Before the operation the IOP was measured in both eyes by using the TonoPen® tonometer (Medtronic Solan) under topical anesthesia (Unicain, 4 mg/ml).

Briefly, for the trabeculectomy a Vicryl 9/0 corneal traction suture was placed superiorly and the eye was pulled down. A limbus-based conjunctival flap was raised after which a blunt dissection of subconjunctival space was performed. After a scleral flap of 5 mm to 5 mm was formed, a piece of the trabecular meshwork was removed and an iridectomy was performed. The conjunctival and scleral flaps were closed by using a Nylon 10-0 suture. At the end of the operation a bleb was formed.

Postoperative follow up of the rabbits took place daily during the first week and two-daily until they were scarified. Examination of both eyes was done and all measurements were performed under topical anesthesia. The IOP-recordings were performed by using a Tono-Pen® tonometer. Bleb characteristics including the bleb area (width and length) and the conjunctival vascularity were investigated according to the Moorfields bleb grading system. During the first week there was an assessment of the anterior segment and of the presence of blood clots around the filtration channel by slit lamp examination.

Example 2

Immunohistochemical Investigation

On day 30 after surgery, rabbits were killed using a lethal intravenous injection of Rompun under general anesthesia.

Both eyes were enucleated, fixed overnight in 4% PFA and embedded in paraffin. Seven-μm thin slides were (immuno-) stained for CD45 to evaluate inflammation and for Sirius red and Trichrome to evaluate fibrosis.

A. Collagen Deposition

Sirius Red and Trichrome staining were used to demonstrate collagen deposition. After Sirius red staining collagen is colored red; after Trichrome staining collagen is colored blue (aniline blue, 5 minutes), nuclei black (Weigert hematoxyline, 10 minutes), and cytoplasm red (Biebrich scarlet fuchsin, 2 minutes).

B. Inflammation

A CD45 staining was performed to study inflammatory cells. After a 20 minutes incubation with methanol and 45 minutes with PIR (1/5; Dakocytomation) the samples were incubated overnight with mouse anti-rabbit CD45 antibody (1/3, 10-50 μg/ml; MCA808; AbDSerotec). The next day the samples were incubated for 45 minutes with RAM-B (1/300; Dakocytomation). The staining was finished by using the Perkin Elmer kit (Renaissance TSA™ Indirect; NEL700). The DAB (Fluka) is giving the tissue a brown color by adding $H_2O_2$. The counterstaining was performed by using Harris hematoxyline (Merck).

Example 3

Effect of Microplasmin on Blebs After Trabeculectomy on Rabbit Eyes

Group 1: Filtration surgery followed by injection in the anterior chamber of microplasmin on day 0: immediately after the trabeculectomy operation 10 rabbits got an anterior chamber injection of microplasmin (200 μl of a solution of 2.5 mg microplasmin/mL in 5 mM citric acid, 6 mg/mL mannitol, pH 3.1). Ten other rabbits underwent trabeculectomy followed by control injections of the same volume of 0.9% NaCl.

Group 2: Filtration surgery followed by administration of topical eye drops containing microplasmin: immediately after the trabeculectomy operation on 3 rabbits, microplasmin was administered in the form of topical eye drops (4 mg microplasmin/mL in 5 mM citric acid, 6 mg/mL mannitol, pH 3.1; 1 drop of ca. 50-55 μL was administered 4 times per day during a period of 14 days). Three other rabbits underwent trabeculectomy followed by administration of control eye drops of 0.9% NaCl.

Group 3: Filtration surgery followed by injection in the anterior chamber of microplasmin and administration of topical eye drops containing microplasmin: immediately after the trabeculectomy operation 5 rabbits got an anterior chamber injection of microplasmin (as in Group 1) combined with administration of topical eye drops (as in Group 2). Five other rabbits underwent trabeculectomy followed by control injections as in Group 1 and administration of control eye drops as in Group 2.

Group 4: similar to Group 1 except that 100 μL microplasmin is administered subconjunctivally (instead of 200 μL in the anterior chamber) in the eyes of 5 rabbits. The control group consists of 5 rabbits.

Group 5: similar to Group 4 except that an additional 100 μL microplasmin is administered subconjunctivally (repeat administration) 1 week after the initial administration. The control group consists of 5 rabbits.

In any of the above outlined experiments the acidic microplasmin solution may alternatively be neutralized prior to contacting with the eye.

Results: As illustrated in FIG. 3 (normalized data), microplasmin significantly augmented the bleb area and survival in a rabbit model of trabeculectomy. All depicted treatments had an initial more or less equal positive effect on the bleb survival (diamonds: topical administration; triangles: anterior chamber injection; squares: combined topical administration and anterior chamber injection). The anterior chamber injection of microplasmin and the combined administration of eye drops and the anterior chamber injection had a positive effect on bleb survival over a longer period of time. Collagen deposition was borderline reduced after microplasmin administration compared to control. No significant changes in inflammation were observed in the anterior chamber or in the conjunctiva. Contrary to the eye drops and/or anterior chamber injection, subconjunctival injection of microplasmin did not result in enhanced bleb survival.

The invention claimed is:

1. A method for treating filtration failure after trabeculectomy surgery of an eye of a human subject, the method comprising administering to the eye of the subject an effective amount of plasmin or an active truncated variant thereof.

2. The method of claim 1, wherein the plasmin or the active truncated variant thereof is in a pharmaceutically acceptable formulation administered to the eye as topical eye drops.

3. The method of claim 1, wherein the plasmin or the active truncated variant thereof is in a pharmaceutically acceptable formulation administered into the anterior chamber of the eye by injection.

4. The method of claim 1, wherein the plasmin or the active truncated variant thereof is administered both by using topical eye drops comprising the plasmin or the active truncated variant thereof and by introduction of the plasmin or the active truncated variant thereof into the anterior chamber of the eye.

5. The method of claim 1, wherein the active truncated variant of plasmin lacks one or more kringle domains.

6. The method of claim 1, wherein the active truncated variant of plasmin is selected from the group consisting of midiplasmin, miniplasmin, microplasmin, and deltaplasmin.

7. The method of claim 1, wherein the trabeculectomy surgery is performed to treat glaucoma in the eye of the subject.

8. The method of claim 1, wherein an effective amount of microplasmin is administered to the eye of the subject.

9. The method of claim 7, wherein an effective amount of microplasmin is administered to the eye of the subject.

10. The method of claim 1, wherein the plasmin or the active truncated version thereof is in a pharmaceutically acceptable formulation further comprising an agent selected from the group consisting of an agent for controlling the intra-ocular pressure, an anti-inflammatory agent, an antiviral agent, an antibacterial agent, an anti-angiogenic agent, an anti-mitotic agent, an antihistamine, an anesthetic, an agent that induces mydriasis, and an agent that induces cycloplegia.

11. The method of claim 1, wherein the active truncated variant of plasmin lacks parts of one or more kringle domains.

12. A method for reducing the occurrence of filtration failure after trabeculectomy surgery of an eye of a human subject, the method comprising administering to the eye of the subject an effective amount of plasmin or an active truncated variant thereof.

13. The method of claim 12, wherein the plasmin or the active truncated variant thereof is in a pharmaceutically acceptable formulation administered to the eye as topical eye drops.

14. The method of claim 12, wherein the plasmin or the active truncated variant thereof is in a pharmaceutically acceptable formulation administered into the anterior chamber of the eye by injection.

15. The method of claim 12, wherein the plasmin or the active truncated variant thereof is administered both by using topical eye drops comprising the plasmin or the active truncated variant thereof and by introduction of the plasmin or the active truncated variant thereof into the anterior chamber of the eye.

16. The method of claim 12, wherein the active truncated variant of plasmin lacks one or more kringle domains.

17. The method of claim 12, wherein the active truncated variant of plasmin lacks parts of one or more kringle domains.

18. The method of claim 12, wherein the active truncated variant of plasmin is selected from the group consisting of midiplasmin, miniplasmin, microplasmin, and deltaplasmin.

19. The method of claim 12, wherein the plasmin or the active truncated version thereof is in a pharmaceutically acceptable formulation further comprising an agent selected from the group consisting of an agent for controlling the intra-ocular pressure, an anti-inflammatory agent, an antiviral agent, an antibacterial agent, an antiviral agent, an anti-angiogenic agent, an anti-mitotic agent, an antihistamine, an anesthetic, an agent that induces mydriasis, and an agent that induces cycloplegia.

20. The method of claim 12, wherein the trabeculectomy surgery is performed to treat glaucoma in the eye of the subject.

21. The method of claim 12, wherein an effective amount of microplasmin is administered to the eye of the subject.

22. The method of claim 20, wherein an effective amount of microplasmin is administered to the eye of the subject.

* * * * *

UNITED STATES PATENT AND TRADEMARK OFFICE
CERTIFICATE OF CORRECTION

PATENT NO. : 8,920,794 B2  
APPLICATION NO. : 13/968775  
DATED : December 30, 2014  
INVENTOR(S) : Jean-Marie Stassen and Ingeborg Stalmans Page 1 of 1

It is certified that error appears in the above-identified patent and that said Letters Patent is hereby corrected as shown below:

Title Page 1, Column 2 References cited (Other Publications), Line 1: Delete "Opthalmology," and insert -- Ophthalmology, --, therefor.

Title Page 1, Column 2 References cited (Other Publications), Line 5: Delete "Opthalmology," and insert -- Ophthalmology, --, therefor.

Title Page 2, Column 2 References cited (Other Publications), Line 13: Delete "deprived" and insert -- derived --, therefor.

Title Page 2, Column 2 References cited (Other Publications), Line 73: Delete "Opthalmol.," and insert -- Ophthalmol., --, therefor.

In the Specification

Column 1, Line 5 (approx.): Delete "CROSSREFERENCE" and insert -- CROSS REFERENCE --, therefor.

In the Claims

Column 18, Line 11 (approx.): In claim 19, delete "agent, an antiviral agent," and insert -- agent, --, therefor.

Signed and Sealed this  
Twenty-first Day of April, 2015

Michelle K. Lee  
*Director of the United States Patent and Trademark Office*